(12) United States Patent
Bartlett et al.

(10) Patent No.: US 8,951,733 B2
(45) Date of Patent: Feb. 10, 2015

(54) METHODS OF POLYNUCLEOTIDE DETECTION

(75) Inventors: Ryan K. Bartlett, O'Fallon, MO (US); Allen T. Christian, Wildwood, MO (US); Mingqi Deng, Chesterfield, MO (US); Sonya J. Franklin, Chesterfield, MO (US); Larry A. Gilbertson, Chesterfield, MO (US); G. David Grothaus, St. Charles, MO (US); R. Douglas Sammons, Wentzville, MO (US); Jianping Xu, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 241 days.

(21) Appl. No.: 13/501,155

(22) PCT Filed: Oct. 15, 2010

(86) PCT No.: PCT/US2010/052779
§ 371 (c)(1),
(2), (4) Date: Aug. 22, 2012

(87) PCT Pub. No.: WO2011/047223
PCT Pub. Date: Apr. 21, 2011

(65) Prior Publication Data
US 2013/0045166 A1 Feb. 21, 2013

Related U.S. Application Data

(60) Provisional application No. 61/252,406, filed on Oct. 16, 2009.

(51) Int. Cl.
*C12Q 1/68* (2006.01)

(52) U.S. Cl.
CPC ........ *C12Q 1/6844* (2013.01); *C12Q 2543/101* (2013.01)
USPC ........................................ 435/6.12; 435/91.2

(58) Field of Classification Search
CPC .. C12Q 1/6844; C12Q 1/6846; C12Q 1/6851; C12Q 1/686
See application file for complete search history.

(56) References Cited

U.S. PATENT DOCUMENTS

| 5,455,166 | A | 10/1995 | Walker |
| 5,470,723 | A | 11/1995 | Walker et al. |
| 5,494,810 | A | 2/1996 | Barany et al. |
| 5,714,320 | A | 2/1998 | Kool |
| 6,235,502 | B1 | 5/2001 | Weissman et al. |
| 6,444,651 | B1 * | 9/2002 | Matsutani et al. ........... 514/44 R |
| 6,743,780 | B1 * | 6/2004 | Hanak et al. ................. 514/44 R |
| 7,282,328 | B2 | 10/2007 | Kong et al. |
| 7,485,428 | B2 | 2/2009 | Armes et al. |
| 7,803,927 | B2 | 9/2010 | Kriz et al. |
| 2004/0077090 | A1 * | 4/2004 | Short ............................ 435/471 |
| 2006/0089332 | A1 * | 4/2006 | Lin et al. .......................... 514/79 |
| 2007/0026514 | A1 * | 2/2007 | Pilla et al. ................... 435/285.1 |
| 2008/0124350 | A1 * | 5/2008 | Mumper et al. ............ 424/184.1 |
| 2008/0184387 | A1 * | 7/2008 | Keetman et al. .............. 800/278 |
| 2008/0242712 | A1 * | 10/2008 | Pershadsingh ................ 514/381 |
| 2008/0249045 | A1 | 10/2008 | Pilauri et al. |

OTHER PUBLICATIONS

Vincent et al, EMBO Reports 5: 795 (2004).*
Barany, "Genetic disease detection and DNA amplification using cloned thermostable ligase," *Proc. Natl. Acad. Sci. USA*; 88:189-193 (1991).
Dean et al., "Comprehensive human genome amplification using multiple displacement amplification," *Proc. Natl. Acad. Sci. USA*; 99:5261-5266 (2002).
Fire et al., "Rolling replication of short DNA circles," *Proc. Natl. Acad. Sci. USA*; 92:4641-4645 (1995).
Guatelli et al., "Isothermal, in vitro amplification of nucleic acids by a multienzyme reaction modeled after retroviral replication," *Proc. Natl. Acad. Sci. USA*; 87:1874-1878 (1990).
Lizardi et al., "Mutation detection and single-molecule counting using isothermal rolling-circle amplification." *Nature Genetics*; 19:225-232 (1998).
Lui et al., "Rolling circle DNA synthesis: small circular oligonucleotides as efficient templates for DNA polymerases," *J. Am. Chem. Soc*; 118:1587-1594 (1996).
Vincent et al., "Helicase-dependent isothermal DNA amplification," *EMBO Reports* 5(8): 795-800(2004).
Walker et al., "Isothermal in vitro amplification of DNA by a restriction enzyme/DNA polymerase system," *Proc. Natl. Acad. Sci. USA*; 88:382-396 (1992).

* cited by examiner

*Primary Examiner* — James Martinell
(74) *Attorney, Agent, or Firm* — Dentons US LLP; Lawrence M. Lavin, Jr.

(57) ABSTRACT

The present invention provides methods of detecting for the presence of a polynucleotide in vivo. These methods are particularly useful for performing identification and/or analysis of samples or specimens in which it is impossible, impractical, or undesirable to move or remove them from their current environment. Methods of practicing the present invention for the purpose of identifying and/or analyzing transgenic plant tissue or cells, in addition to animal tissue or cells and bacterial cells are also provided.

10 Claims, 6 Drawing Sheets

METHODS OF POLYNUCLEOTIDE DETECTION

CROSS REFERENCE TO RELATED APPLICATIONS

This application claims benefit to U.S. provisional application Ser. No. 61/252,406, filed 16 Oct. 2009, and serial number PCTUS201052779, filed 15 Oct. 2010 which is herein incorporated by reference.

INCORPORATION OF SEQUENCE LISTING

The sequence listing that is contained in the file named "38-21-(56800)0001txt", which is 4.14 kilobytes as measured in Microsoft Windows operating system and was created on 4 Apr. 2012, is filed electronically herewith and incorporated herein by reference.

FIELD OF THE INVENTION

The present invention discloses methods for detecting a polynucleotide. More specifically it relates to methods of in vivo polynucleotide detection.

BACKGROUND

Methods for analyzing nucleic acids by isolating and amplifying nucleic acid sequences in vitro are widely known and used in research, forensics, medicine and agriculture. One of the best-known amplification methods is the polymerase chain reaction (PCR), which is a target amplification method. The development of isothermal nucleic acid target amplification technologies circumvents the need for expensive instrumented thermal cyclers required for PCR. Such methods include, but are not limited to, the Recombinase Polymerase Amplification (RPA) method (see for example U.S. Pat. No. 7,485,428); Strand Displacement Amplification (SDA), (See for example, U.S. Pat. Nos. 5,455,166 and 5,470,723); Transcription-Mediated Amplification (TMA), (See for example, Guatelli eta., *Proc. Natl. Acad. Sci. USA* 87:1874-1878 (1990)); Rolling Circle Amplification (RCA), (See for example, Fire and Xu, *Proc. Natl. Acad Sci. USA* 92:4641-4645 (1995); Lui, et al., *J. Am. Chem. Soc.* 118:1587-1594 (1996); Lizardi, et al., *Nature Genetics* 19:225-232 (1998), U.S. Pat. Nos. 5,714,320 and 6,235,502); Helicase Dependant Amplification (HDA), (see for example Vincent et al., *EMBO Reports* 5(8): 795-800 (2004); U.S. Pat. No. 7,282,328); and Multiple Displacement Amplification (MDA) (See for example Dean et. al., *Proc. Natl. Acad Sci. USA* 99:5261-5266 (2002)).

Although nucleic acid amplification and detection technologies have improved, the current methods still perpetuate the basic paradigm of performing the main steps (nucleic acid isolation, amplification, and detection or analysis) in vitro, in a reaction tube or vessel. In vitro analysis first requires steps to acquire a sample of the target material, for example tissue or cells before performing nucleic acid isolation, amplification, and detection steps. In high throughput situations where numerous samples are needed, the sampling process can become a time, labor, or ergonomic burden, not to mention increasing the use of consumable laboratory supplies and the possibility of error due to cross contamination with other samples, or a mix-up in sample identification. In other situations, laboratory facilities and/or equipment may not be readily available, for example where it is impossible, impractical, or undesirable to move or remove samples or specimens from their current environment. In other situations, sample destruction may be undesirable, such as in the case of museum artifact or specimen testing. Worse, in other situations involving live animal subjects, obtaining a sample can be invasive and/or painful. Therefore, a method in which isolation, amplification, and detection or analysis of nucleic acids are performed without the need for sampling or processing target tissue or cells in a closed system or reaction well is desirable.

SUMMARY OF THE INVENTION

The present invention provides methods of detecting for the presence of a polynucleotide in an organism comprising topically applying an isothermal polynucleotide amplification agent in vivo to a polynucleotide exposed on the surface of said organism.

In practicing these methods, the organism may be a eukaryotic organism such as an animal, a plant, a fungus, or an alga. The organism may also be a prokaryotic organism such as a bacterium. In embodiments where the organism is a plant, it may be a transgenic plant.

The method of the present invention further comprises applying a detecting agent to the surface of said organism for said detecting. In some embodiments, the detection agent comprises a labeled hybridization probe for detecting said polynucleotide. The method of polynucleotide detection may further comprise fluorescence, colorimetric, luminescence, or radioactivity.

The invention also provides methods of exposing said polynucleotide on the surface of said organism. In certain aspects, a cell at the surface of said organism is lysed to provide said polynucleotide exposed on the surface of said organism. In certain embodiments, said cell is lysed by topically applying an alkaline solution, an acidic solution, a surfactant, or a physical treatment to said cell. In one embodiment, the alkaline solution may be a NaOH or a KOH solution. In another embodiment, the surfactant may be a Polysorbate-20 solution. In yet another embodiment, the physical treatment may comprise abrading, rubbing, sanding, scraping, scratching, cutting, piercing, sonicating, or poking. In another embodiment, the physical treatment may comprise various naturally occurring environmental damage or disease.

Also provided are methods of practicing the present invention for the purpose of identifying and/or analyzing transgenic plant tissue. The methods of identifying transgenic plant tissue further comprise first introducing in the plant a recombinant DNA or RNA sequence with a transgene, then growing the plant to at least the R0 stage, and then topically applying an isothermal polynucleotide amplification agent in vivo to a polynucleotide exposed on the surface of the plant, and detecting for the presence of said transgene. In one embodiment, the methods of the present invention may be used to identify a transgenic plant in which there is no marker gene present.

Also provided are methods of practicing the present invention for the purpose of identifying and/or analyzing an animal tissue or cell. In one embodiment, said animal tissue or cell may be of a human. The methods of analyzing the animal tissue or cell further comprise detecting for the presence of a polynucleotide by topically applying an isothermal polynucleotide amplification agent in vivo to a polynucleotide exposed on the surface of said animal tissue or cell and detecting for the presence of said polynucleotide. In certain non-limiting embodiments, the polynucleotide can be a naturally occurring, wild type, or genomic DNA, RNA or cDNA sequence, the mutation or alteration of which can indicate the presence or predisposition of a pathology, disease or disorder.

Additionally provided herein are methods of practicing the present invention for the purpose of identifying and/or analyzing bacterial cells, wherein said bacterial cells comprise one or more bacterial colonies. The methods of analyzing bacterial cells further comprises detecting for the presence of a polynucleotide by topically applying an isothermal polynucleotide amplification agent in vivo to a polynucleotide exposed on said bacterial cells; and detecting for the presence of said polynucleotide.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings:

FIG. 5a shows the RPA reaction performed at 39° C. FIG. 5b shows the RPA reaction performed at 37° C. FIG. 5c shows the RPA reaction performed at 33° C. FIG. 5d shows the RPA reaction performed at 30° C.

DETAILED DESCRIPTION

Figure 1:
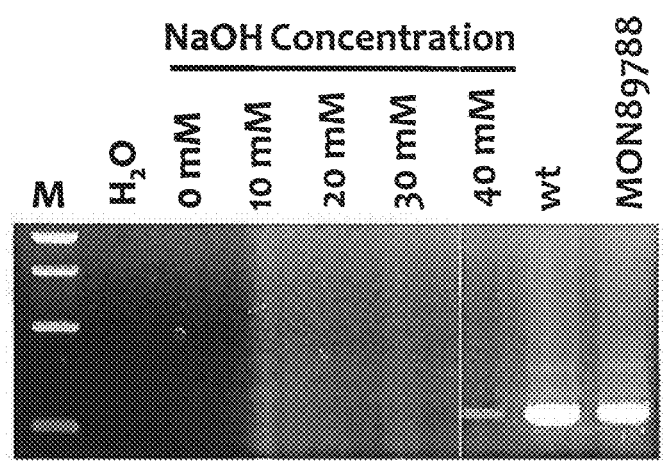
FIG. 1 illustrates successful PCR amplification and subsequent detection by gel electrophoreses of a single copy gene from genomic DNA obtained by topical application of lyses solutions containing various concentrations of Sodium Hydroxide (NaOH) to the surface of a detached leaf. The expected PCR product size is 501 bp. M: markers DNA; wt: amplified GmTub1 gene from wild type soybean DNA; MON89788: amplified GmTub1 gene from transgenic soy event of the same name.

The following is a detailed description of the invention provided to aid those skilled in the art in practicing the present invention. Those of ordinary skill in the art may make modifications and variations in the embodiments described herein without departing from the spirit or scope of the present invention. Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Unless otherwise noted, conventional methods are used for these procedures, such as those provided in the art and various general references. Where a term is provided in the singular, the inventors also contemplate aspects of the invention described by the plural of that term. Where there are discrepancies in terms and definitions used in references that are incorporated by reference, the terms used in this application shall have the definitions given herein. Other technical terms used herein have their ordinary meaning in the art that they are used in, as exemplified by a variety of technical dictionaries. The inventors do not intend to be limited to a mechanism or mode of action. Reference thereto is provided for illustrative purposes only.

The present invention discloses methods for detecting a polynucleotide. More specifically it provides methods for performing, either individually or in combination, the steps of exposing (if necessary), amplifying, and detecting or analyzing a polynucleotide in an organism in vivo. In certain aspects of the present invention, application of these methods for detecting the presence of a polynucleotide in various organisms is provided.

Such methods are useful in rapidly identifying a transgenic plant by detecting the presence of a target polynucleotide such as a gene of interest (GOI) or other genetic elements in an expression cassette from a population of non-transgenic plants. The rapid identification of a transgenic plant enables the faster development of a commercial product. It also provides easier, nucleotide specific identification of transgenic plant tissue in the field, or in plant material processing equipment, or repository facilities such as grain elevators. The methods of the present invention are also useful in rapid detection, diagnosis or prognosis of a pathology, syndrome, disease or disorder, genetically related or otherwise acquired, in humans or animals. More rapid identification of such conditions will aid care providers in providing treatment.

In describing and claiming the disclosed subject matter, the following terminology will be used in accordance with the definitions set forth below, unless indicated otherwise. These definitions are further exemplified within the example portion of this disclosure.

As used herein, the term "in vivo" refers to that which occurs or is made to occur within or on tissue, or within or on at least one cell of an organism, wherein said cell or tissue is not removed or separated from overall organism of which it is a part, and wherein said cell or tissue is not fixed on a medium or other matrix, such as a slide, and wherein the reagents used for the exposure, amplification and detection or analysis of a polynucleotide are topically applied to said cell or tissue.

As used herein, the term "polynucleotide" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompass a polynucleotide as defined above. In addition, polynucleotide as used herein may include triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term "exposed polynucleotide" refers to any polynucleotide that is available for amplification and/or detection methods due to lysis of the cell from which it originates. Methods of cell lysis are known in the art, such as chemical means including but not limited to contact with an alkaline solution, a surfactant, or acidic solution; and physical means including but not limited to abrading, rubbing, scraping, scratching, cutting, piercing, sonicating, or poking. Some of these cell lysing events may occur naturally in the environment.

As used herein, the term "topical application" or variations such as "topically applying" or "topically applied" generally refers to contacting a cell or tissue sample with a desired agent, for example a polynucleotide detection agent or cell lysing agent, such that the cell or tissue itself serves as a means of retaining all or some said agent. It is understood that topical application of an agent may result in both surface and subsurface exposure to said agent.

As used herein, the term "polynucleotide amplification agent" or "nucleic acid amplification" or variations thereof generally refers to any number of compositions, or reactions thereof, known in the art that involve replication and amplification of a template polynucleotide wherein a second strand of a nucleic acid molecule is synthesized using a first strand as a template. The term includes, for example, PCR and related methods and isothermal amplification. These compositions typically comprise a polymerase or fragment thereof or combination of polymerases having specified activity, dNTPs, a template polynucleotide (DNA or RNA), oligonucleotide primers (in most reactions), and an appropriate reaction buffer (e.g., Tris-HCl, with $MgCl_2$, for Taq DNA polymerase).

As used herein, the term "primer" refers to a short segment of DNA or DNA-containing nucleic acid molecule, which (i) anneals under amplification conditions to a suitable portion of a DNA or RNA sequence to be amplified (e.g. a target sequence), and (ii) initiates extension, and is itself physically extended, via polymerase-mediated synthesis.

As used herein, the term "isothermal" as it pertains to amplification or reactions, refers to processes that occur at a constant temperature (in the case of helicase dependant amplification (HDA), this does not include the single brief time period (less than 15 minutes) at the initiation of amplification which may be conducted at the same temperature as the amplification procedure or at a higher temperature). Moreover, the term "constant temperature" refers to an amplification reaction that is carried out under isothermal conditions as opposed to thermo cycling conditions. Constant temperature procedures rely on methods other than heat to denature the DNA, such as the strand displacement ability of some polymerases or of DNA helicases that act as accessory proteins for some DNA polymerases. Thus, the term "constant temperature" does not mean that no temperature fluctuation occurs, but rather indicates that the temperature variation during the amplification process is not sufficiently great that it provides the predominant mechanism to denature product/template hybrids. The constant temperature can be less than 60° C., less than 50° C., less than 45° C., and can even be less than 40° C.

As used herein, the term "detection agent" generally refers to any number of compositions or reactions thereof known in the art that involve facilitating the detection of a target polynucleotide. In certain aspects, facilitation of target polynucleotide detection involves the use of a nucleic acid probe or primer labeled with a detectable marker. Detectable markers include but are not limited to, an enzyme, an isotope, or a fluorophore.

As used herein, the term "target nucleic acid sequence" refers to a nucleic acid sequence of interest, for example, a nucleic acid sequence to be amplified, detected, or measured according to the methods herein, or to be amplified, detected, or measured through the use of the devices of the invention, or the kits of the invention. Target nucleic acid sequences, also referred to herein sometimes as "targets", "target sequences", "target nucleic acids", "target polynucleotide", or "target molecules" comprise a sequence that hybridizes with at least one primer when contacted therewith (e.g. under the conditions for amplification and detection), or is at least partially complementary to at least one primer. A target sequence can be either an entire molecule or a portion thereof. Also, it is to be understood that the use of the term "target nucleic acid sequence" with respect to detection of a particular trait does not necessarily mean that the target sequence must comprise or define the trait itself—i.e. in certain embodiments, the presence of the target sequence may be associated with a particular trait or quality, in other embodiments the trait or quality may be associated with the absence of the target sequence. For example a particular disease trait may be either associated with the presence of a mutated sequence, or with the absence of, or a decrease in wild-type sequence. Still other traits may be associated with an abundance or excess of a wild-type sequence. Similarly, in cases where a particular RNA or protein are encoded by a particular sequence, the target nucleic acid selection may either be in the coding or the noncoding strand of the corresponding DNA, for example, for reasons of preferred or convenient sites, such as recognition or cleavage sites within one or the other sequence. The skilled artisan will appreciate the assays and methods provided herein are flexible with respect to the design and selection of particular target nucleic acid sequences based on the particular application as well as the convenience or preference of the artisan developing the application.

As used herein, the term "cell(s)" or "tissue" may refer to many different non-limiting embodiments. Representative cells include, but are not limited to eukaryotic cells such as animal cells, plant cells, fungal cells or algal cells. In some embodiments, representative cells may also include prokaryotic cells such as bacterial cells. Animal cells include but are not limited to stem cells, germ cells, pluripotent cells, totipotent cells, undifferentiated cells, epidermal cells, endodermal cells, mesenchymal cells, ectodermal cells, brain cells, skin cells, heart cells, bone marrow cells, blood cells, lymphocytes, adipose cells, smooth muscle cells, muscle cells, osteoclasts, osteoblasts, macrophage, T-cells, helper T-cells, among others. Plant cells include but are not limited to dermal cells, leaf cells, root cells, petiole cells, chloroplasts, seed cells, cotyledon cells, hypocotyl cells, epicotyl cells, mesocotyl cells, coleoptile cells, plumule cells, stem cells, embryonic cells, flower cells including stamen, pollen, petal, sepal, pistil, pollen tube, ovule and receptacle, among others. It is understood that the inventors contemplate the methods of the present invention to be carried out on any cells or tissue which the detection agent(s) can be applied, in the disclosed manner.

As used herein, the term "transgenic plant," "transformed plant," or "transgenic event" (or variations thereof) refers to a plant or progeny thereof derived from a transformed plant cell or protoplast wherein an alteration of the plant DNA sequence is produced, and wherein said alteration comprises the introduction, deletion, suppression, mutation, or overexpression of an exogenous or endogenous DNA molecule, resulting in a genetic profile that is not 100% homologous to a native, non-transgenic plant of the same species. It will be understood by one of ordinary skill in the art that this definition applies even when the altered or introduced DNA molecule is not expressed.

As used herein, the term "transgene" refers to a polynucleotide that produces a change in the DNA sequence of an organism. "Transgene" may refer to an exogenous polynucleotide that is introduced into the plant, but may also refer to an endogenous polynucleotide in which an alteration such as a deletion, suppression, mutation, or overexpression has been produced.

As used herein, the term "transformation" refers to a process of producing a transgenic plant.

As used herein, the term "R0" refers to any plant regenerated through tissue culture, including a transgenic plant.

As used herein, the term "R1" refers to the first progeny of a cross between R0 parents, including one or more transgenic parents.

The present invention describes a method of in vivo isothermal amplification of a polynucleotide, wherein an isothermal amplification agent is topically applied to an exposed polynucleotide on the surface of an organism.

Any method for exposing nucleic acid molecules from tissue or cells that provide nucleic acid molecules of sufficient purity to be captured by a hybridization probe or to be amplified can be used.

In one embodiment, polynucleotide exposure is achieved by cell lysis by topically applying an alkaline solution, an acidic solution, or a surfactant to the surface of the cells or tissue of an organism. In another embodiment, polynucleotide exposure is achieved by cell lysis by topically applying a solution of Sodium Hydroxide (NaOH) and Polysorbate 20 (commercially available as Tween-20; SigmaAldrich, CAS No: 9005-64-5) onto a cell or tissue of interest, such as plant or animal tissue for a period of time in the ranges including but not limited to 5 to 60 minutes, 1 to 2 hours, 2 to 12 hours, and 12 to 24 hours. In certain non-limiting aspects, the solution may be prepared with NaOH at a concentration ranging from 10 to 200 mM, including but not limited to about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, and 200.

In another aspect, a solution of Potassium Hydroxide (KOH) at a concentration of about 1 to 120 mM is topically applied, including about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, and 120.

In another aspect, a surfactant such as Tween-20 may be topically applied alone to achieve cell lysis, for example at a concentration of, but not limited to, 0.05% in solution. Other surfactants such as Triton X-100 or NP40 can be optionally added to the NaOH or KOH to aid the release of the DNA from the cells. It will be understood by those of ordinary skill in the art that the above embodiments may be performed using solutions comprising effective concentrations beyond the ranges provided without departing from the scope of the present invention.

Other methods for lysing cells comprise a physical treatment, including but not limited to abrading, rubbing, scraping, scratching, cutting, piercing, sonicating, or poking, and can be done prior to, during, after, or as an alternative to application of NaOH or KOH solutions, or other non-limiting cell lysis methods. In general, one of ordinary skill in the art will appreciate that the key feature of any method polynucleotide exposure is that the genomic DNA or RNA provided by the cell lysis is not fragmented to a degree that would preclude detection of the polynucleotide of interest.

In some aspects, cell lysis may occur naturally. In plant tissue, some non-limiting examples of natural cell lysis are lesions or damage caused by disease, blight, insect, environmental conditions, or natural cell degradation. In animal tissue, some non-limiting examples of natural cell lysis are lesions or damage caused by disease, infection, exposure to certain environmental conditions, or natural cell degradation. In such cases, one may opt to forego application of a specific cell lysing agent or method, and instead apply the subsequent amplification and detection agents directly to the damaged area.

In the present invention, polynucleotide amplification is done isothermally. One example of an isothermal amplification method include is Recombinase Polymerase Amplification (RPA), (see for example U.S. Pat. No. 7,485,428) wherein a recombinase agent is contacted with a first and a second nucleic acid primer to form a first and a second nucleoprotein primer. Second, the first and second nucleoprotein primers are contacted to a double stranded target sequence to form a first double stranded structure at a first portion of said first strand and form a double stranded structure at a second portion of said second strand so the 3' ends of said first nucleic acid primer and said second nucleic acid primer are oriented towards each other on a given template DNA molecule. Third, the 3' end of said first and second nucleoprotein primers are extended by DNA polymerases to generate first and second double stranded nucleic acids, and first and second displaced strands of nucleic acid. Finally, the second and third steps are repeated until a desired degree of amplification is reached. In certain non-limiting embodiments, the RPA reaction is conducted at temperatures between 30 and 39 degrees Celsius. Another isothermal amplification method is Strand Displacement Amplification (SDA). SDA combines the ability of a restriction endonuclease to nick the unmodified strand of its target DNA and the action of an exonuclease-deficient DNA polymerase to extend the 3' end at the nick and displace the downstream DNA strand. The displaced strand serves as a template for an antisense reaction and vice versa, resulting in exponential amplification of the target DNA (See, for example, U.S. Pat. Nos. 5,455,166 and 5,470,723). In the originally-designed SDA, the DNA was first cleaved by a restriction enzyme in order to generate an amplifiable target fragment with defined 5' and 3'-ends but the requirement of a restriction enzyme cleavage site limited the choice of target DNA sequences (See for example, Walker et. al., *Proc. Natl. Acad. Sci. USA* 89:392-396 (1992)). This inconvenience has been circumvented by the utilization of bumper primers which flank the region to be amplified (Walker et al. supra (1992)). SDA technology has been used mainly for clinical diagnosis of infectious diseases such as chlamydia and gonorrhea. One of the most attractive features of SDA is its operation at a single temperature which circumvents the need for expensive instrumented thermal cycling.

Another isothermal amplification method, Transcription-Mediated Amplification (TMA), (See for example, Guatelli eta., *Proc. Natl. Acad. Sci. USA* 87:1874-1878 (1990)), utilizes the function of an RNA polymerase to make RNA from a promoter engineered in the primer region, and a reverse transcriptase, to produce DNA from the RNA templates. This RNA amplification technology has been further improved by introducing a third enzymatic activity, RNase H, to remove the RNA from cDNA without the heat-denaturing step. Thus the thermo-cycling step has been eliminated, generating an isothermal amplification method named Self-Sustained Sequence Replication (3SR) (See, for example, Guatelli eta., *Proc. Natl. Acad. Sci. USA* 87:1874-1878 (1990)). However, the starting material for TMA and 3SR is limited to RNA molecules.

Yet another isothermal amplification method is Rolling Circle Amplification (RCA), (See, for example, Fire and Xu, *Proc. Natl. Acad Sci. USA* 92:4641-4645 (1995); Lui, et al., *J. Am. Chem. Soc.* 118:1587-1594 (1996); Lizardi, et al., *Nature Genetics* 19:225-232 (1998), U.S. Pat. Nos. 5,714,320 and 6,235,502). RCA generates multiple copies of a sequence for the use in in vitro DNA amplification adapted from in vivo rolling circle DNA replication In this reaction, a DNA polymerase extends a primer on a circular template generating tandemly linked copies of the complementary sequence of the template (See, for example, Kornberg and Baker, DNA Replication, W. H. Freeman and Company, New York ($2^{nd}$ ed. (1992)). Recently, RCA has been further developed in a technique, named Multiple Displacement Amplification (MDA), which generates a highly uniform representation in whole genome amplification (See, for example, Dean et. al., *Proc. Natl. Acad Sci. USA* 99:5261-5266 (2002)).

The isothermal amplification method known as Helicase Dependant Amplification (HDA), (see for example Vincent et al., *EMBO Reports* 5(8): 795-800 (2004); U.S. Pat. No. 7,282,328) uses a DNA helicase to separate double-stranded DNA and generate single-stranded templates for primer hybridization and subsequent extension. Because the DNA helicase unwinds dsDNA enzymatically, the initial heat denaturation and subsequent thermocycling steps are not required.

Additional nucleic acid amplification methods include Ligase Chain Reaction (LCR), which is a probe amplification technology (See, for example, Barany, *Proc. Natl. Acad Sci. USA* 88:189-193 (1991)); and U.S. Pat. No. 5,494,810).

In one aspect of the invention, detection of the amplified polynucleotide is facilitated by application of a detection agent. A detection agent may be a nucleic acid probe or primer labeled with a detectable marker, topically applied concurrently, or subsequently to the isothermal amplification agents. In certain embodiments, the amplification agent and detection agent may be one in the same, when the amplification primers themselves contain detectable markers. Detectable markers include but are not limited to, an enzyme, an isotope, a fluorophore, a lanthanide, a hapten, radioactive labels such as $^{32}P$, $^{35}S$, $^{3}H$, and the like, or enzymatic markers that produce detectable signals when a particular chemical reaction is conducted, such as alkaline phosphatase or horseradish peroxidase. Labeling of oligonucleotide probes with fluorescent labels can be accomplished as described in U.S. Pat. No. 6,838,244 or other references cited therein.

When the nucleic acid probe is labeled with a hapten, it can be detected and quantitated by a coupling molecule that binds the hapten and permits detection. Coupling molecules that permit detection include, but are not limited to, antibodies, antibodies conjugated to enzymes, antibodies that are detectably labeled, antibodies labeled with fluorescent molecules, aptamers that recognize the hapten and other proteinaceous molecules that recognize the hapten. Haptens include, but are not limited to, biotin, digoxigenin, and the like that can be covalent linked to the nucleic acid probe. Proteinaceous molecules that recognize haptens include, but are not limited to, proteins such as streptavidin. In these hybridization-based assays, the amount of detectably labeled probe that is hybridized to the distinct polynucleotide is determined to provide a measurement of the amount of that distinct polynucleotide in the sample.

In some aspects, amplification and detection of more than one target polynucleotide (multiplexing) is accomplished by using at least two probe sets specific for different target polynucleotides. In one embodiment, the reporter for the probe specific for a first target polynucleotide provides a different detectable signal than the reporter for the acceptor probe specific for the second target polynucleotide. For example, one reporter can have a detectable signal at one wavelength, and the other reporter can have a detectable signal at a different wavelength. The presence of a detectable signal from either reporter or the combined detectable signal of both reporters is indicative of the presence and optionally the location of the respective target polynucleotides. The movement of target polynucleotides over a period of time can also be tracked and visualized using the disclosed probes and probe sets.

One non-limiting aspect of the present invention provides application of the methods for identifying and/or analyzing transgenic plants, including any product, seed, tissue, or cells derived thereof. More specifically, the methods of the present invention can be used to identify a transgenic plant amongst a population on non-transgenic plants. Even more specifically, the methods of the present invention may be used to identify a transgenic plant in which there is no marker gene present.

The construction of expression cassettes for use in transforming monocotyledonous plants or dicotyledonous plants is well established. Expression cassettes are DNA constructs where various promoter, coding, and polyadenylation sequences are operably linked. In general, expression cassettes typically comprise a promoter that is operably linked to a sequence of interest which is operably linked to a polyadenylation or terminator region. In certain instances including, but not limited to, the expression of transgenes in monocot plants, it may also be useful to include an intron sequence. When an intron sequence is included, it is typically placed in the 5' untranslated leader region of the transgene. In certain instances, it may also be useful to incorporate specific 5' untranslated sequences in a transgene to enhance transcript stability or to promote efficient translation of the transcript.

Plant expression cassettes comprising genes of interest, selectable markers and/or scoreable markers can be introduced into the chromosomes of a host plant via methods such as *Agrobacterium*-mediated transformation, *Rhizobium*-mediated transformation, *Sinorhizobium*-mediated transformation, particle-mediated transformation, DNA transfection, DNA electroporation, or "whiskers"-mediated transformation. Suitable methods for transformation of plants include any method by which DNA can be introduced into a cell, such as by electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,824,877; 5,591,616; 5,981,840; and 6,384,301; and protoplast transformation as illustrated in U.S. Pat. No. 5,508,184, etc. Aforementioned methods of introducing transgenes are well known to those skilled in the art and are described in U.S. Patent Application Publication No. 20050289673 (*Agrobacterium*-mediated transformation of corn), U.S. Pat. No. 7,002,058 (*Agrobacterium*-mediated transformation of soybean), U.S. Pat. No. 6,365,807 (particle mediated transformation of rice), and U.S. Pat. No. 5,004,863 (*Agrobacterium*-mediated transformation of cotton). Through the application of techniques such as these, the cells of virtually any plant species may be stably transformed, and these cells developed into transgenic plants. Other techniques that may be particularly useful in the context of cotton transformation are disclosed in U.S. Pat. Nos. 5,846,797, 5,159,135, 6,624,344, U.S. Patent Application Nos. 2009/0138985 and 2008/0256667; and techniques for transforming *Brassica* plants in particular are disclosed, for example, in U.S. Pat. No. 5,750,871; and techniques for transforming soybean are disclosed in for example in Zhang et al., *Plant Cell Tiss Org Cult.* 56: 37-46. (1999), and U.S. Pat. No. 6,384,301; techniques for transforming corn are disclosed in WO9506722; techniques for transforming sugarcane are disclosed in U.S. Patent Application Publication 2004/0123342. Methods of using bacteria such as *Rhizobium* or *Sinorhizobium* to transform plants are described in Broothaerts, et al., Nature. 2005, 433:629-33 and US Patent Application No. US2007/0271627: Methods for transforming other plants can be found in Compendium of Transgenic Crop Plants, 2009. Blackwell Publishing.

Transgenic plants are typically obtained by co-introduction of the gene of interest and a selectable gene into a plant cell, a plant tissue or a plant by any one of the methods described above, and regenerating or otherwise recovering the transgenic plant under conditions requiring expression of said selectable marker gene for plant growth. The selectable marker gene can be a gene encoding a neomycin phosphotransferase protein, a phosphinothricin acetyltransferase protein, a glyphosate resistant 5-enol-pyruvylshikimate-3-phosphate synthase (EPSPS) protein, a hygromycin phosphotransferase protein, a dihydropteroate synthase protein, a sulfonylurea insensitive acetolactate synthase protein, an atrazine insensitive Q protein, a nitrilase protein capable of degrading bromoxynil, a dehalogenase protein capable of degrading dalapon, a 2,4-dichlorophenoxyacetate monoxygenase protein, a methotrexate insensitive dihydrofolate reductase protein, and an aminoethylcysteine insensitive octopine synthase protein. The corresponding selective agents used in conjunction with each gene can be: neomycin (for neomycin phosphotransferase protein selection), phosphinothricin (for phosphinothricin acetyltransferase protein selection), glyphosate (for glyphosate resistant 5-enol-pyruvylshikimate-3-phosphate synthase (EPSPS) protein selection), hygromycin (for hygromycin phosphotransferase protein selection), sulfadiazine (for a dihydropteroate synthase protein selection), chlorsulfuron (for a sulfonylurea insensitive acetolactate synthase protein selection), atrazine (for an atrazine insensitive Q protein selection), bromoxinyl (for a nitrilase protein selection), dalapon (for a dehalogenase protein selection), 2,4-dichlorophenoxyacetic acid (for a 2,4-dichlorophenoxyacetate monoxygenase protein selection), methotrexate (for a methotrexate insensitive dihydrofolate reductase protein selection), or aminoethylcysteine (for an aminoethylcysteine insensitive octopine synthase protein selection).

Transgenic plants can also be obtained by co-introduction of a gene of interest and a scoreable marker gene into a plant cell by any one of the methods described above, and regenerating the transgenic plants from transformed plant cells that test positive for expression of the scoreable marker gene. Scoreable marker genes are any genes that provide for simple destructive or non-destructive expression assays. The scoreable marker gene can be a gene encoding a beta-glucuronidase protein, a green fluorescent protein, a yellow fluorescent protein, a red fluorescent protein, a beta-galactosidase protein, a luciferase protein derived from a luc gene, a luciferase protein derived from a lux gene, a sialidase protein, streptomycin phosphotransferase protein, a nopaline synthase protein, an octopine synthase protein or a chloramphenicol acetyl transferase protein.

Genes of interest include, but are both limited to, genes that provide an agronomic trait comprising herbicide tolerance, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress tolerance, increased digestibility, industrial enzyme production, pharmaceutical peptides and small molecule production, improved processing traits, proteins improved flavor, nitrogen fixation, hybrid seed production, reduced allergenicity, biopolymers, or biofuel production.

When the expression vector is introduced into a plant cell or plant tissue, the transformed cells or tissues are typically regenerated into whole plants by culturing these cells or tissues under conditions that promote the formation of a whole plant (i.e., the process of regenerating leaves, stems, roots, and, in certain plants, reproductive tissues). The development or regeneration of transgenic plants from either single plant protoplasts or various explants is well known in the art Horsch, R. B. et al. *Science* 227:1229-1231; (1985). This regeneration and growth process typically includes the steps of selection of transformed cells and culturing selected cells under conditions that will yield rooted plantlets. This initial regenerated plant or plantlet are referred to as an "$R_0$" plant, while subsequent generations of plants derived from that "$R_0$" plant are referred to as "$R_1$", "$R_2$", "$R_2$" or "$R_x$" plants, where "x" is the generation number of the plant relative to the initial regenerated parent. The resulting transgenic rooted shoots are thereafter planted in an appropriate plant growth medium such as soil.

Alternatively, transgenes can also be introduced into isolated plant shoot meristems and plants regenerated without going through callus stage tissue culture (U.S. Pat. No. 7,002,058). When the transgene is introduced directly into a plant, or more specifically into the meristematic tissue of a plant, seed can be harvested from the plant and selected or scored for presence of the transgene.

Transgenic plants expressing genes of interest contemplated herein include, but are not limited to, barley, corn, oat, rice, rye, sorghum, turf grass, sugarcane, wheat, alfalfa, banana, broccoli, bean, cabbage, canola, carrot, cassava, cauliflower, celery, citrus, clover, coconut, coffee, cotton, a cucurbit, Douglas fir, eggplant, eucalyptus, flax, garlic, grape, olive, onion, loblolly pine, melons, palm, lettuce, pea, peanut, pepper, potato, poplar, pine, radish, sunflower, safflower, soybean, strawberry, sugar beet, sweet gum, sweet potato, switch grass, tea, tobacco, tomato, triticale, turf grass, watermelon, ornamental, shrub, nut, chickpea, pigeon pea, millets, hops, and pasture grass plants.

Single copy, selectable marker free transgenic plants are ideal for trait commercialization. Thus, it is important that the insertion sites for the GOI and the marker genes be far enough apart, physically, within the plant's genome that they can be segregated away from one another during a plant breeding process. The production of a marker-free transgenic plant is thus determined by the two separate DNA linkage patterns. If the GOI and marker gene are integrated together in same genomic locus, they are linked and transmitted to progeny together. Only when the two DNAs are inserted into different chromosomes or unlinked locus, can a marker free plant be produced by segregation in progeny. The generation and selection of high quality commercial events are thus dependent on delivery of two unlinked DNA fragments, one containing GOI traits, the other the selectable marker. Typically, assessing whether the GOI and the marker are linked requires a time-consuming molecular characterization process, such as Invader™, (Third Wave, Technologies, Madison, Wis.), or Southern hybridization (*J Mol Biol.*, 98:503-517.). Although the commonly used methods of plant transformation typically include steps aimed at reducing the frequency with which the undesirable extraneous sequences have integrated into the plant genome, those steps occasionally fail. Because time and resources, plus greenhouse and field space are expensive, it is highly desirable to produce a transgenic plant without the use of a marker gene, thereby eliminating the need for linkage assays. Thus a rapid assay that could determine the presence of the GOI at an R0 stage is also desirable. Another embodiment of the present invention is a nucleic acid specific assay involving amplification and detection of a target polynucleotide, performed on R0 plant tissue to identify a plant that has been successfully transformed, even when there is no marker gene present, amongst a population of non-transgenic plants, said assay being performed either in vivo.

Any of the aforementioned genetic elements of the transgene or expression cassette can be used to devise appropriate hybridization probes or amplification primers for identification of a transgenic plant using methods of the present invention. Various oligonucleotides suitable for complementing certain polynucleotide sequences that are frequently found in transgenic plants are also described in U.S. Patent Application Publication 20060127889. Primer design parameters (oligonucleotide length, GC content, etc) for RPA technology are described in Piepenburg, O., Williams, C. H., Stemple, D. L., Armes, N. A. *PLoS Biology* Vol. 4, No. 7, e204 (2006).

In the case of transgenic plant species that reproduce sexually, seeds can be collected from plants that have been "selfed" (self-pollinated) or out-crossed (i.e., used as a pollen donor or recipient) to establish and maintain the transgenic plant line. Transgenic plants that do not sexually reproduce can be vegetatively propagated to establish and maintain the transgenic plant line. As used herein, transgenic plant line refers to transgenic plants derived from a transformation event where the transgene has inserted into one or more locations in the plant genome. In a related aspect, the methods of the present invention can also be applied to a seed produced by the transformed plant, a progeny from such seed, and a seed produced by the progeny of the original transgenic plant, produced in accordance with the above process. Such progeny and seeds will have a gene of interest stably incorporated into their genome, and such progeny plants will inherit the traits afforded by the introduction of a stable transgene in Mendelian fashion.

The methods of the present invention can be applied to any transgenic plant of any generation. However, it is particularly advantageous to apply the methods of the invention to "R0" plants or plantlets as the information obtained can be used to cull undesirable non-transgenic events from a population. The sample used in the methods of this invention can be obtained from any portion of the transgenic plant including, but not limited to, the leaf, root, flower, stem, or any combination thereof.

In another aspect, the present invention enables a plant to be assayed for resistance, immunity, or susceptibility to plant disease such fungal, nematodes, and bacterial diseases. In another aspect, the present invention enables a plant to be assayed for resistance, immunity, or susceptibility to animal diseases.

Any naturally occurring or non-naturally occurring nucleic acid that is suitable for amplification can be a target nucleic acid sequence for use herein. The target polynucleotide can be genomic, including but not limited to all of the resident genetic information in a host such as the host chromosome, cDNA or mRNA, the genomes of sub-cellular organelles (i.e. mitochondrial or plastid genomes), artificial chromosomes, or extra-chromosomal elements which may be either natural or synthetic in origin. The target nucleic acid sequence may be from a human, animal, plant, mycoplasma, or microorganism in certain embodiments. In various embodiments, the target nucleic acid sequence is present in human cells or tissue. Accordingly, appropriate nucleic acid amplification primers and/or probes that are used in accordance to the methods of the present invention are particularly useful as diagnostic tools in diagnosis or prognosis of a pathology, syndrome, disease or disorder. For example, a probe sequence that is complementary to a polynucleotide sequence that is distinctive to an infectious disease agent, including but not limited to viruses, bacteria, parasites, and fungi, will indicate the presence of the infectious agent in a patient. The target polynucleotide can also be a naturally occurring, wild type, or genomic DNA, RNA or cDNA sequence, the mutation or alteration of which can indicate the presence or predisposition of a pathology, disease or disorder. Generally, a healthy organism expresses a target polynucleotide having a first sequence. An organism having a pathology or predisposition of a pathology typically expresses a variation of the target polynucleotide. The variation of the target polynucleotide includes deletions, mutations, substitutions, transpositions, translocations, insertions, inversions, single-nucleotide polymorphisms, and combinations thereof. The presence of the target nucleic acid sequence in the sample is indicative of a genetic disorder in one embodiment, in another embodiment, the absence of a target is an indication of such a disorder. In some instances, an organism having a pathology or predisposition of a pathology may not express a target polynucleotide, express reduced levels of the target polynucleotide, or express excessive levels of the target polynucleotide compared to levels of the target polynucleotide expressed by a healthy organism.

The methods are also applicable to a variety of other diagnostic applications. For example, such methods may be useful in testing for suspected accidental or intentional release of any of a broad array of different etiological agents. Samples for use in the methods provided herein may be derived from any source, and the methods provided are particularly well-suited for samples which are clinical, forensic, environmental, agricultural, or veterinary in terms of their origin or source. Such broad categories are not mutually exclusive as the skilled artisan will recognize, for example a sample taken from a farm where animals are raised may be deemed environmental, agricultural, or veterinary depending on the circumstances. The disclosure of certain of such sources is not to the exclusion of others for use herein, but rather is to help inform as to examples of the samples suitable for use with the instant methods.

In another aspect, the methods of the present invention provide a useful screening tool for drug discovery where a rapid specific and sensitive assay can detect in vivo changes in the expression, suppression, mutation, or interaction of polynucleotides of interest, either at a steady state or in response to the administration of drug candidates.

Yet another embodiment of the present invention provides a novel approach to detecting for the presence of a polynucleotide in a bacterial colony. The controlled culturing of bacterial colonies on a growth medium is will known in the art. Also known in the art is the practice of using genetically altered bacteria to express a particular gene of interest thus producing a particular protein of interest, such as human insulin in *E. coli*. (see for example U.S. Pat. No. 4,704,362) or using *Agrobacterium* as a vector for plant transformation as described in U.S. Pat. Nos. 5,824,877; 5,591,616; 5,981,840; and 6,384,301. Using the methods of the present invention, the appropriate cell lysis, amplification and detection agents are topically applied directly to a bacterial colony within the culture plate in which it is presently growing.

EXAMPLES

Those of skill in the art will appreciate the many advantages of the methods and compositions provided by the present invention. The following examples are included to demonstrate certain embodiments of the invention. Those of skill in the art should, in light of the present disclosure, appreciate that many changes can be made in the specific embodiments that are disclosed and still obtain a like or similar result without departing from the spirit and scope of the invention. All references cited herein are incorporated herein by reference to the extent that they supplement, explain, provide a background for, or teach methodology, techniques, or compositions employed herein.

Example 1

Surface Exposure of a Polynucleotide by NaOH Mediated Cell Lysis Followed by Amplification and Detection The tissues used in this example were detached from their plants, as this served as a preliminary experiment to demonstrate successful DNA obtainment for amplification and detection by NaOH mediated cell lysis performed by topical application of NaOH to the surface of leaf tissue in support of doing the same in vivo. One milliliter of a lysis solution containing various concentrations of NaOH and 0.05% Tween-20 was topically applied to different leaves of a soybean plant and left for 20 minutes at room temperature. The solution was then transferred from the leaf surface to a tube and neutralized with 200 µl of 3M sodium acetate, pH5.2. The DNA was coprecipitated with 1 ul of 5 mg/mL glycogen and one volume (1 mL) of isopropanol. The precipitate was resuspended in 20 microliters of Tris EDTA (TE) buffer. Two microliters of the DNA solution was used for PCR amplification of a single copy endogenous *Glycine max* tubulin1 (GmTub1) gene from soybean genome. The PCR results in FIG. 1 show that a leaf treated with 40 mM NaOH releases sufficient DNA for amplification by PCR. The primers used for the amplification were GmTub1-F2: TCTCAACAACAATGAGCGGAGT (SEQ ID NO. 1) and GmTub1-R2: GCAAGAAGGCCTTTCTCTTGAA (SEQ ID NO. 2).

Example 2

Recombinase Polymerase Amplification (RPA) Surface-Exposed DNA

Figure 2:
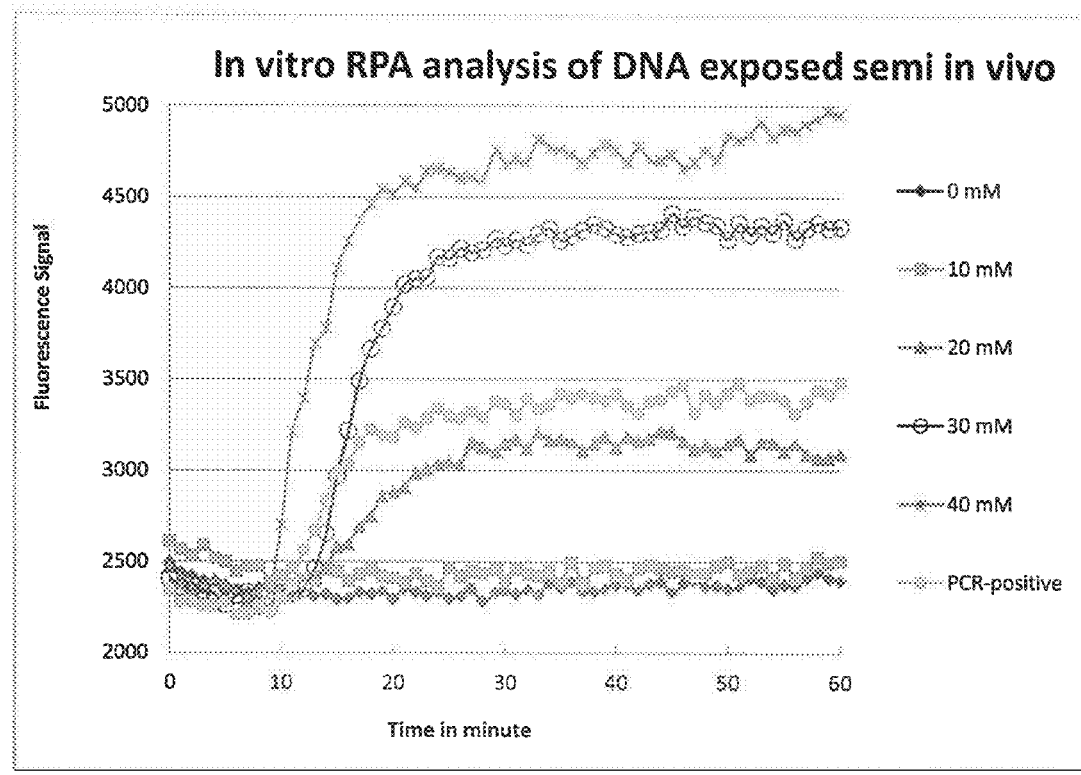
FIG. 2 illustrates successful Recombinase Polymerase Amplification of a single copy gene from genomic DNA prepared from a detached leaf treated with lysis solutions containing various concentrations of NaOH.

This example demonstrates recombinase polymerase amplification of the DNA preparation obtained in Example 1. One microliter of DNA sample was added to 49 µl of RPA mix, which was made by adding 49 µl of Rehydration Buffer consisting of 41.8 µl water, 3.75 µl PEG35k (20% w/v in water), 1 µl Potassium Acetate (5M), 1.75 µl Tris/Acetate (1M, pH8.3), and 0.7 µl Magnesium Acetate (1M) to the freeze dried RPA reaction derived from 36.145 ul water, 5 µl 10× buffer, 2.5 µl Creatine Kinase (2 mg/ml in water), 1.4 µl uvsX, 0.16 µl uvsY, 1.9 µl gp32, 3.5 µl MON89788Y forward primer (6 µM), 3.5 µl MON89788 reverse primer (6 µM), 1.5 µl soybean lectin forward primer (6 µM), 1.5 µl soybean lectin reverse primer (6 µM), 1 µl MON89788Y probe (6 µM; Tamra), 1 µl Soy lectin probe (6 µM; FAM), 10 µl PEG35k (20% w/v in water), 6 µl Trehalose (50% w/v in water), 0.125 µl ExonucleaseIII (10022-1-H2,3), 0.27 µl SAu polymerase (10026-1-H1,2), 2.5 µl E-mix (50 mM ATP, 1M PhosphCreatine; in water), and 2 µl dNTPs (6 mM each). The sequences of the primers and probes were: Soy lectin forward primer: ccagaatgtggttgtatctctctccctaacctt (SEQ ID NO. 3); Soy lectin reverse primer: cccgaggaggtcacaatagcgtctccttggag (SEQ ID NO. 4); Soy lectin probe, 5'-ggaaactgtttctttcagctggaacaagFtHg1gccgaagcaacc-3' (SEQ ID NO. 5), where F=dT-Fluorescein, 1=dT1Black-Hole-Quencher-1, H=THF (d-spacer) and 3' block was C3 spacer; MON89788 forward primer: CCCTCTTGGCTTTTCTAAGTTTGAGCTCGTTACT (SEQ ID NO. 6); MON89788 reverse primer: CCCGCCTTCAGTTTAAACTATCAGTGTTTGG (SEQ ID NO. 7) and MON89788 probe: 5'-cccgccttcagtttaaactatcagtgtttggagc2tHaRaaccacgattgaag-3'(SEQ ID NO. 8), where R=dT-TAMRA, 2=dT-Black-Hole-Quencher-2, H=THF (d-spacer) and 3' block was C3 spacer. Fluorescein and TAMRA are florescence reporters. The reactions were conducted and the florescence intensity was measured at 39° C. using a BMG Microplate Reader (see FIG. 2).

Example 3

Figure 3:
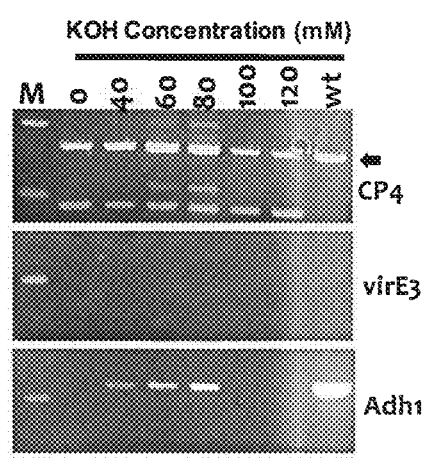
FIG. 3 illustrates successful PCR amplification of a transgene, CP4, *Agrobacterium* virE3, and a corn endogenous Adh1 sequence, and subsequent detection by gel electrophoreses by topically applying lysis solutions containing various concentrations of KOH to the surface of a detached corn leaf.

Surface Exposure of a Polynucleotide by KOH Mediated Cell Lysis Followed by Amplification and Detection The tissues used in this example were detached from their plants, as this served as a preliminary experiment to demonstrate the use of a different lysis solution for exposing DNA on the surface of tissue in support of doing the same in vivo. A lysis solution containing various concentrations of KOH from 0 to 120 mM, and 0.05% Tween was used to extract DNA from the leaves of tissue-cultured corn plants that had undergone transformation procedures with *Agrobacterium*. One milliliter of the lysis solutions were applied to different leaves of corn plants overnight. The lysis solution was then neutralized with 200 µl sodium acetate, pH5.2. The DNA was coprecipitated with 1 µl of 5 mg/mL glycogen and one volume (1 mL) of isopropanol. Three genes: a gene of interest (CP4), *Agrobacterium* VirE3 gene, and a corn endogenous gene, a corn alcohol dehydrogenase1 (Zm.ADH1) were targeted for PCR amplification. Primers OsAct-I-F (5' CTG CTT CGT CAG GCT TAG ATG T 3' (SEQ ID NO. 9)) and CP4-R-seq2 (5' GTC TTC CGA TTT CAC CTG CAC (SEQ ID NO. 10)) were used for CP4 detection. An expected 828 by amplified DNA band was seen on the gel. For *Agrobacterium* endogenous virE3 detection, primers virE3-F1 (5' TGA AGA GGA GGC AAC AAG GAA T (SEQ ID NO. 11)) and virE3-R1 (CCT TTT CGA CGG GTT AGT TCA C (SEQ ID NO. 12)) were used. An expected 501 bp amplified DNA band was seen on the gel. Zm.Adh1 gene was used as an internal control with an expected size of 599 bp amplified DNA band on the gel. The primers were Zm.Adh1-F1 (5' ACA GTG GTA CTG CCC GTG TCT A 3' (SEQ ID NO. 13)) and Zm.Adh1-R1 (5' TCA CCA GTT ACG AAA CCA ATC G 3' (SEQ ID NO. 14)). As FIG. 3 demonstrates, DNA could be amplified from leaves treated with all KOH concentrations tested, including 0 mM indicating that Tween-20 alone can adequately lyse cells and expose sufficient DNA for the reaction. The VirE3 gene was not amplified, indicating that the CP4 signal was not an artifact of *Agrobacterium* presence.

Example 4

Figure 4:
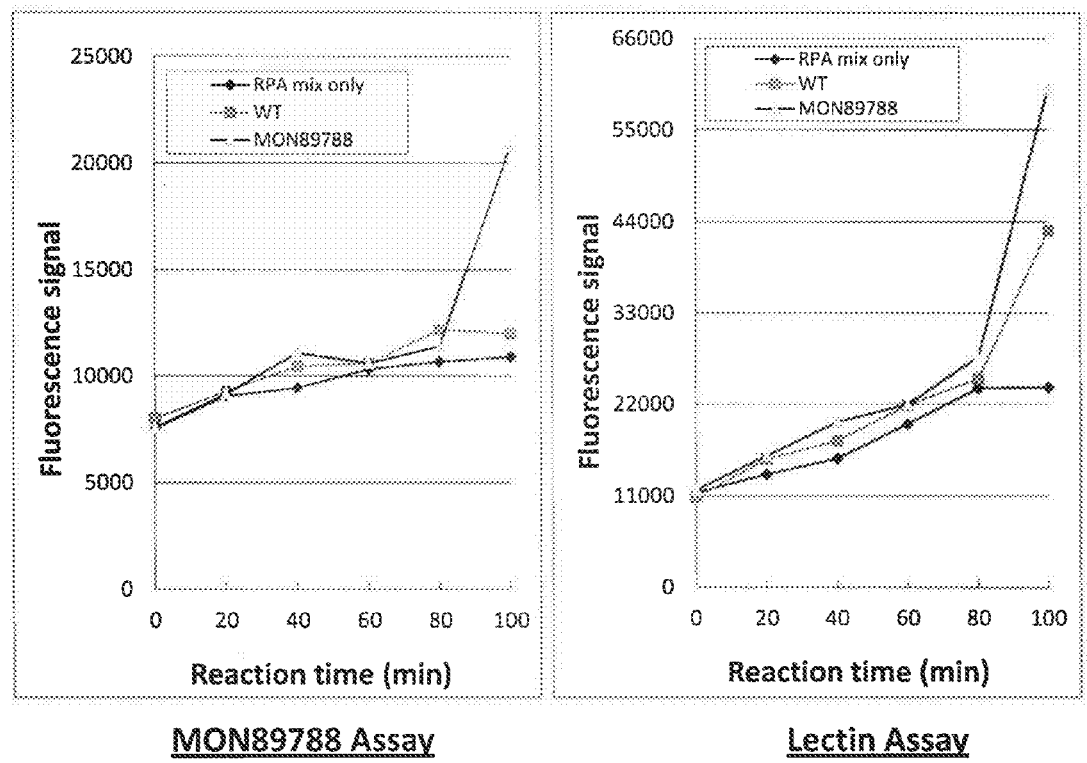
FIG. 4 illustrates successful in vivo cell lysis and DNA exposure, followed by in vivo recombinase polymerase amplification of an event specific gene sequence from transgenic soy event MON89788, and endogenous soybean lectin gene, followed by in vitro detection of the target polynucleotide by fluorescence.

In Vivo Nucleic Acid Exposure by NaOH Mediated Cell Lysis Followed by In Vivo RPA on the Surface of a Living Leaf Attached to a Plant To make plant genomic DNA accessible to RPA reactions, 100 μl of 0.2N NaOH plus 0.5% Tween-20 was applied to either transgenic soybean event MON89788, or wild type leaves in vivo, while still attached to the plants of which they were a part. The plants were kept at room temperature for 10 min. Sodium hydroxide solution was removed and then the treated leaves were air dried at 37° C. To conduct RPA reactions on attached leaves of living plants, one hundred microliters of RPA mix containing primers and probes for identification of an event-specific MON89788 sequence, and endogenous soybean lectin gene was applied to the NaOH-treated sites (see Example 2 for primer sequences). The whole plants were then moved into an incubator at 37° C. Ten microliter aliquots of the RPA reaction were taken from the leaves at 20 minute intervals to measure florescence intensity. As shown in FIG. 4, on leaves that received only RPA reagents (no pre-treatment with NaOH), DNA amplification was not observed. Soybean lectin gene was detected in the RPA reactions on both MON89788 and wild type leaves. As expected, the event-specific MON89788 sequence was detected only in the RPA reactions on the MON89788 transgenic leaves.

Example 5

In Vivo Nucleic Acid Exposure and Amplification Via Spray Application of Reagents This example demonstrates nucleic acid exposure via cell lysis on plant leaf tissue, performed in vivo, while the leaf is still attached to the plant of which it is a part. KOH or NaOH solution as described in Example 3 and 4 (are applied by spray at different concentrations ranging from 0 to 100 mM) to corn leaf tissue. The leaves are then optionally sprayed with 200 μM acetic acid to neutralize the high pH of KOH or NaOH to avoid interference of KOH or NaOH with the RPA reagents. Before amplifying the exposed DNA, a fluorescent image of the leaf is captured using imaging technology with filters that are appropriate for detection of the probe fluorophors, e.g. Fam (emission at 520 nm) or Tamara (emission at 590 nm). This image is recorded as "time 0". Amplification of the exposed DNA is then conducted by spraying the RPA reagent mixture directly on the leaf. Detection of the amplified DNA is done by imaging the leaf at different time interval using a CCD camera under fluorescent light. Higher fluorescence intensity from leaves indicate the amplification of targeted nucleic acid sequence.

Example 6

RPA Reaction at Different Temperatures

Figure 5:
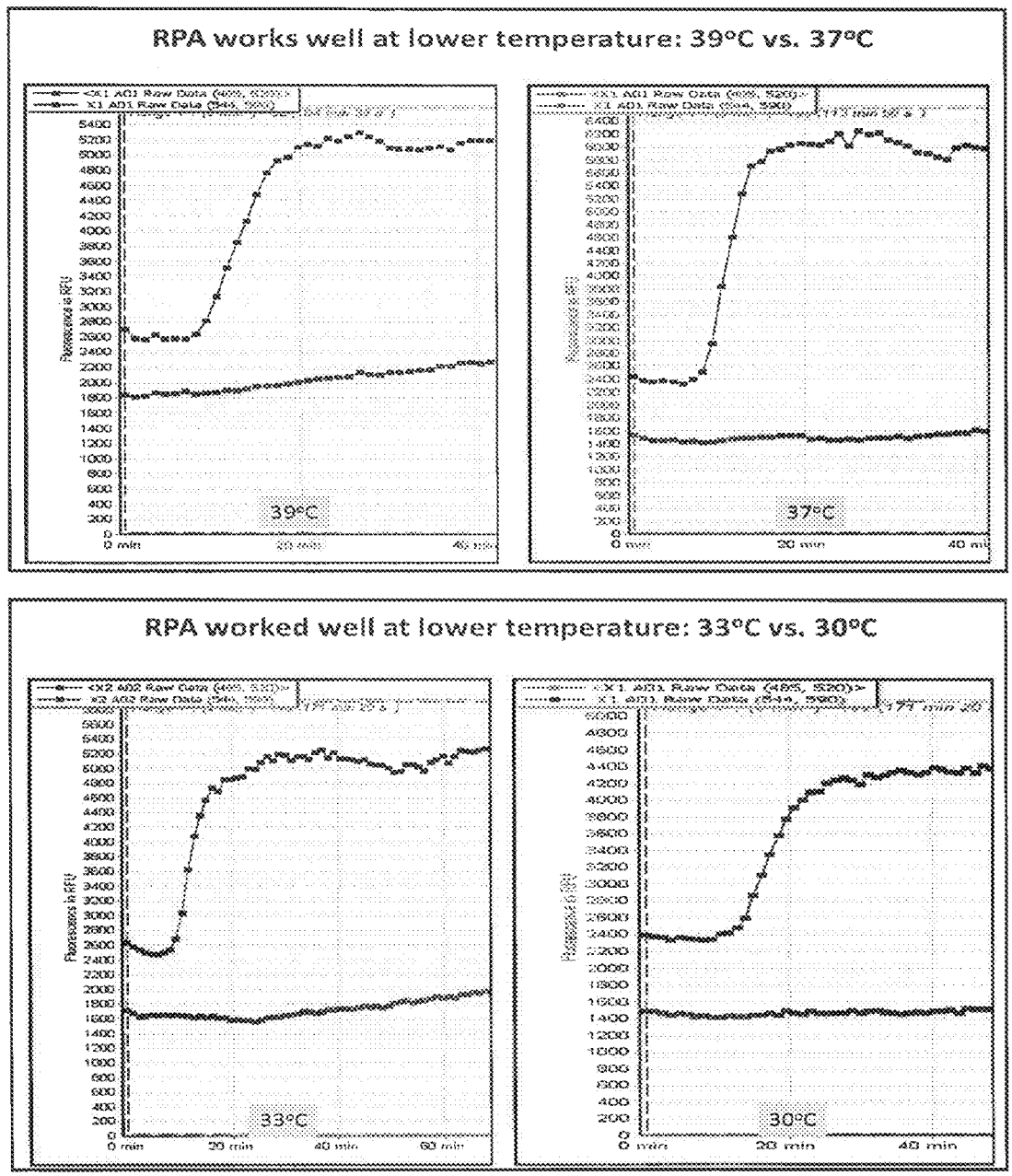
FIG. 5 illustrates that the RPA reaction can be successfully performed at various temperatures.

This example demonstrates that the RPA reaction can be performed at various temperatures. A leaf disc from a fresh MON89788 soy plant was treated with 250 μl of 0.2N NaOH for 10 min. One microliter of the lysate was used as a template in 50 μl RPA reactions as described in example 2. The reactions were then incubated at different temperature and kinetic readings of fluorescence were taken with a microplate reader. The results indicated that RPA reaction was successful at all temperatures tested. As shown in FIG. 5, MON89788-specific signal spiked between 0 and 20 minutes for all temperature treatments. The plateau phase was reached in approximately 40 minutes at 30 C, approximately 20 min at 39 C or 37 C, and approximately 30 min at 33 C.

Example 7

In Vivo Nucleic Acid Exposure, Amplification, and Detection

This example demonstrates nucleic acid exposure, amplification and detection, all performed on the surface of plant leaf tissue. The tissues used in this example were detached from their plants, as this served as a preliminary experiment to demonstrate successful detection of RPA products on the surface of leaf tissue in support of doing the same in vivo. Soybean leaves were sprayed with ~40 μl 0.2M NaOH and incubated at 37° C. for ~15 minutes and allowed to dry. Leaves were then sprayed with ~20 μl of RPA reagents, as described in Example 2, except with soy oLB and tubulin instead of soy lectin and MON89788. Sequences for oLB and tubulin primers and probes were as follows: oLB forward primer: 5' CCC CCA TTT GGA CGT GAA TGT AGA CAC GTC G 3' (SEQ ID NO. 15); oLB reverse primer: 5' CGA CAA ATT ACG ATC CGT CGT ATT TAT AGG CG 3'(SEQ ID NO. 16); oLB Probe: 5' GAC ACG TCG AAA TAA AGA TTT CCG AAT-(dT-FAM)-AG-(THF)-A-(dT-BHQ-1)-AAT TTG TTT ATT G 3'-(Biotin TEG) (SEQ ID NO. 17); Tubulin forward primer: 5' TTC CGA ACA CTC AAG CTC ACA AAT CCA AGT TG 3' (SEQ ID NO. 18); Tubulin reverse primer: 5' CCC ATG AAG GTG GAG GAC ATG GAC AAA CCC G 3' (SEQ ID NO. 19); Tubulin probe: 5'CAA CGT ACA GAA CAA GAA CTC CTC CTA C-(dT-TAMRA)-T-(THF)-G-(dT-BHQ-2)-GGA GTG GAT CCC G3'-(Biotin TEG) (SEQ ID NO. 20).

Figure 6:
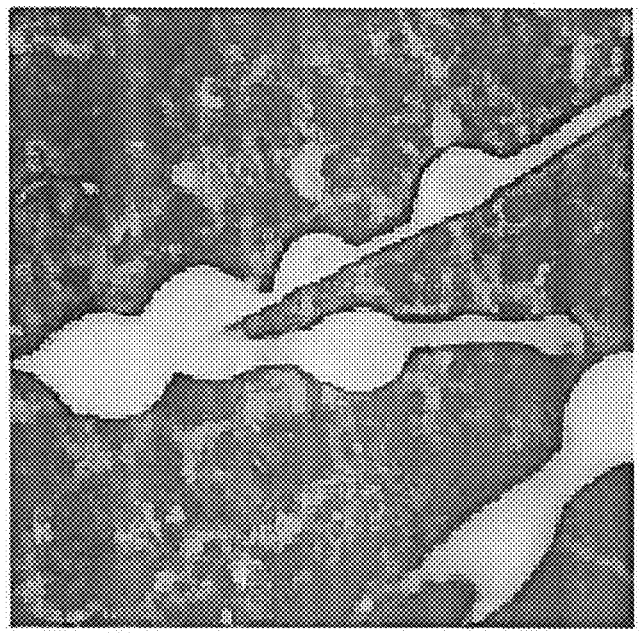
FIG. 6 illustrates successful fluorescent detection of an RPA reaction performed on the surface of leaf tissue.

Leaves were incubated at 37° C. for ~60 minutes. The RPA reaction was then confirmed with hyperspectral confocal fluorescence imaging of the leaves. Leaves were placed on the stage of a hyperspectral confocal microscope. No mounting medium was added, nor was any additional sectioning of the leaves, or placement of glass over the samples performed. Image acquisition was performed using the hyperspectral confocal microscope with a 488 nm laser for excitation (Coherent, Inc.) and the entire emission spectra was detected from 500-800 nm. The hyperspectral image was processed using Sandia National Laboratories proprietary multivariate curve resolution (MCR) software (see M C Pedroso et al. Hyperspectral Confocal Fluorescence Microscope: A New Look into the Cell. Microscopy Today, Volume 18 (05): pp 14-18; Published online by Cambridge University Press Aug. 24, 2010). RBG images produced with hyperspectral confocal microscope and MCR show the fluorescence of RPA product on the leaf (FIG. 6) where the dark shade indicates chlorophylls in tissue, and the light shade indicates fluorescing RPA product in the trichome cells.

Example 8

In Vivo Nucleic Acid Exposure and Amplification of Bacterial Colony

This example demonstrates application of the present invention for polynucleotide detection in bacterial colonies. Bacterial colonies are treated with NaOH, in a range from 2 mM to 200 mM for a range of time from 5 minutes to 60 minutes, to release DNA for the RPA reaction. RPA reagents with suitable primer/probe combinations for specific polynucleotide sequence detection are then applied, either directly to the colony in a small volume (e.g. 1 µl) or as a spray across the entire plate. Colonies are incubated for 30 to 60 minutes, at temperatures ranging from 30 degrees C. to 42 degrees C. A fluorescence imaging system is used to monitor for an increase in fluorescence across the entire plate, thus identifying colonies with a time dependent increase in fluorescence, and thus the presence of the polynucleotide of interest.

What is claimed is:

1. A method of detecting for the presence of a polynucleotide in an organism comprising topically applying an isothermal polynucleotide amplification agent in vivo to a polynucleotide exposed on the surface of said organism and detecting the presence of said polynucleotide, wherein said isothermal polynucleotide amplification agent is not a template polynucleotide.

2. The method of claim 1 wherein said organism is a plant.

3. The method of claim 2 wherein said plant is a transgenic plant and said polynucleotide is recombinant DNA or RNA transcribed therefrom.

4. The method of claim 3 wherein said recombinant DNA or RNA in said transgenic plant is selectable marker-free and scoreable marker-free.

5. The method of claim 1 wherein said organism is an animal.

6. The method of claim 1 wherein said organism is a bacterium.

7. The method of claim 1 further comprising applying a detecting agent to the surface of said organism for said detecting.

8. The method of claim 1 wherein a cell at the surface of said organism is lysed to provide said polynucleotide exposed on the surface of said organism.

9. The method of claim 8 wherein said cell is lysed by topically applying an alkaline solution, an acidic solution, a surfactant, or a physical treatment to said cell.

10. The method of claim 1 wherein said isothermal polynucleotide amplification agent comprises recombinase and polymerase.

* * * * *

```
                              SEQUENCE LISTING

<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
tctcaacaac aatgagcgga gt                                               22

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
gcaagaaggc ctttctcttg aa                                               22

<210> SEQ ID NO 3
<211> LENGTH: 33
<212> TYPE: DNA
<213> ORGANISM: Artificial Sequence
<220> FEATURE:
<223> OTHER INFORMATION: Primer

<400> SEQUENCE: 3
ccagaatgtg gttgtatctc tctccctaac ctt                                   33

<210> SEQ ID NO 4
<211> LENGTH: 32
<212> TYPE: DNA
<213> ORGANISM: Artificial Sequence
<220> FEATURE:
<223> OTHER INFORMATION: Primer

<400> SEQUENCE: 4
cccgaggagg tcacaatagc gtctccttgg ag                                    32

<210> SEQ ID NO 5
<211> LENGTH: 45
<212> TYPE: DNA
<213> ORGANISM: Artificial Sequence
<220> FEATURE:
<223> OTHER INFORMATION: Probe

<400> SEQUENCE: 5
ggaaactgtt tctttcagct ggaacaagtt agtgccgaag caacc                      45

<210> SEQ ID NO 6
<211> LENGTH: 35
<212> TYPE: DNA
<213> ORGANISM: Artificial Sequence
<220> FEATURE:
<223> OTHER INFORMATION: Primer
```

```
<400> SEQUENCE: 6
ccctcttggc ttttctaagt ttgagctcgt tactg                           35

<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
cccgccttca gtttaaacta tcagtgtttg g                               31

<210> SEQ ID NO 8
<211> LENGTH: 53
<212> TYPE: DNA
<213> ORGANISM: Artificial Sequence
<220> FEATURE:
<223> OTHER INFORMATION: Probe

<400> SEQUENCE: 8
cccgccttca gtttaaacta tcagtgtttg gagcttgata accacgattg aag       53

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
ctgcttcgtc aggcttagat gt                                         22

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
gtcttccgat ttcacctgca c                                          21

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
tgaagaggag gcaacaagga at                                         22

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
ccttttcgac gggttagttc ac                                         22
```

```
<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
acagtggtac tgcccgtgtc ta                                              22

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
tcaccagtta cgaaaccaat cg                                              22
```